United States Patent [19]

Knöfel et al.

[11] Patent Number: 4,786,751

[45] Date of Patent: Nov. 22, 1988

[54] DIISOCYANATES, DIISOCYANATE MIXTURES AND A PROCESS FOR THEIR PRODUCTION

[75] Inventors: Hartmut Knöfel, Odenthal; Michael Brockelt, Bergisch-Gladbach; Stefan Penninger; Herbert Stutz, both of Dormagen, all of Fed. Rep. of Germany

[73] Assignee: Bayer Aktiengesellschaft, Leverkusen, Fed. Rep. of Germany

[21] Appl. No.: 797,072

[22] Filed: Nov. 12, 1985

Related U.S. Application Data

[63] Continuation of Ser. No. 556,521, Nov. 30, 1983, abandoned.

[30] Foreign Application Priority Data

Dec. 8, 1982 [DE] Fed. Rep. of Germany ....... 3245321

[51] Int. Cl.⁴ .................... C07C 71/00; C08G 18/10
[52] U.S. Cl. ........................... 560/358; 528/44; 528/48; 528/49; 528/55; 528/58; 528/59; 528/60; 528/76; 528/77; 528/85
[58] Field of Search .................. 260/453 A, 453 AM; 560/358

[56] References Cited

U.S. PATENT DOCUMENTS

3,663,514 5/1972 Campbell et al. .......... 260/77.5 AT

*Primary Examiner*—Alan Siegel

*Attorney, Agent, or Firm*—Gene Harsh; Joseph C. Gil; Lyndanne M. Whalen

[57] ABSTRACT

Diisocyanates and isomeric mixtures of diisocyanates corresponding to the formula

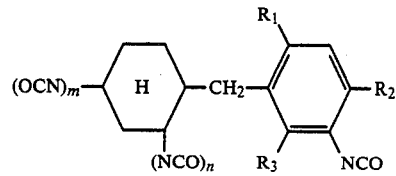

in which $R_1$, $R_2$, $R_3$, m and n are as defined herein are made by phosgenating diamines corresponding to the formula

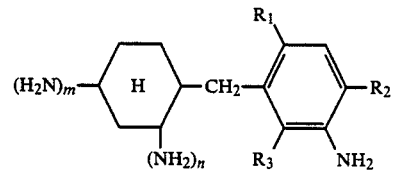

in which $R_1$, $R_2$, $R_3$, m and n are as defined herein at a temperature of from $-20°$ to $250°$ C. These diisocyanates are particularly useful as starting materials for the production of polyurethanes by the isocyanate polyaddition process.

10 Claims, No Drawings

DIISOCYANATES, DIISOCYANATE MIXTURES AND A PROCESS FOR THEIR PRODUCTION

This is a continuation of application Ser. No. 556,521, filed Nov. 30, 1983, abandoned.

BACKGROUND OF THE INVENTION

This invention relates to new isocyanatobenzylcyclohexyl isocyanates which are mono-substituted on the aromatic ring, optionally in the form of isomeric mixtures. The present invention also relates to a process for the production of such isocyanates by the phosgenation of the underlying diamines or diamine mixtures.

Asymmetric diisocyanates having an aromatically bound and a cycloaliphatically bound isocyanate group would be eminently suitable for the production of polyurethanes by the prepolymer process due to the wide difference in reactivity between these isocyanate groups. The more highly reactive, aromatically bound isocyanate group would be the first to react, forming the isocyanate prepolymer, which would then react in a second stage to form the high molecular weight polyurethane.

Such asymmetric diisocyanates would also be suitable for the preparation of modified isocyanates, as for example, uretdione diisocyanates. The more highly reactive isocyanate group would react in the first reaction stage and undergo dimerization to form a diisocyanate containing uretdione groups. This modified diisocyanate could then be reacted with compounds containing isocyanate reactive groups.

U.S. Pat. No. 3,663,514 describes one such diisocyanate, namely 4-(4-isocyanatobenzyl)cyclohexyl isocyanate. This diisocyanate has not been used to any great extent because the diamine from which this diisocyanate is produced is only obtainable in yields of less than 35% of theoretical by asymmetric hydrogenation on the nucleus. Consequently, the pure asymmetric diisocyanate can only be obtained after elaborate purification.

SUMMARY OF THE INVENTION

It is an object of the present invention to provide new diisocyanates having aromatically and cycloaliphatically bound isocyanate groups.

It is also an object of the present invention to provide diisocyanates having aromatically and cycloaliphatically bound isocyanate groups which diisocyanates are liquid or have a low viscosity at room temperature.

It is another object of the present invention to provide diisocyanates having aromatically and cycloaliphatically bound isocyanate groups which would be particularly useful in the production of polyurethanes due to their solubility and compatibility with reactants containing hydroxyl groups.

It is yet another object of the present invention to provide a process for the production of diisocyanates having aromatically and cycloaliphatically bound isocyanate groups in high yields.

It is a further object of the present invention to provide a process for the production of diisocyanates having aromatically and cycloaliphatically bound isocyanate groups in a manner such that only minor amounts of contaminating unhydrogenated or perhydrogenated diisocyanates are present.

These and other objects which will be apparent to those skilled in the art are accomplished by phosgenating diamines corresponding to the formula

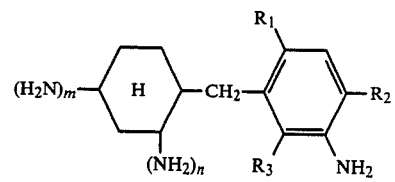

in which $R_1$, $R_2$, $R_3$, m and n are as defined below.

DETAILED DESCRIPTION OF THE INVENTION

The present invention relates to diisocyanates corresponding to the formula

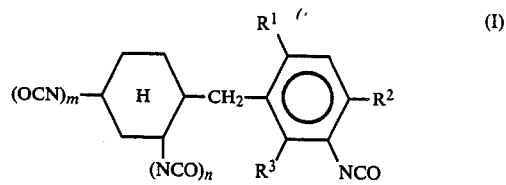

optionally in the form of isomeric mixtures and optionally in admixture with minor quantities of the corresponding perhydrogenated diisocyanates and/or with minor quantities of the corresponding unhydrogenated aromatic diisocyanates.

In the above formula, $R^1$, $R^2$ and $R^3$ which may be identical or different each represents hydrogen or (optionally branched) alkyl groups having 1–12 carbon atoms, with the restriction that two of the groups $R^1$, $R^2$ and $R^3$ are hydrogen, and m and n each represents 0 or 1 under the condition that the sum of $m+n=1$, and when either m or $n=0$ the free valency is saturated by hydrogen.

The invention also relates to a process for the preparation of these diisocyanates or diisocyanate mixtures, characterized in that diamines corresponding to the formula

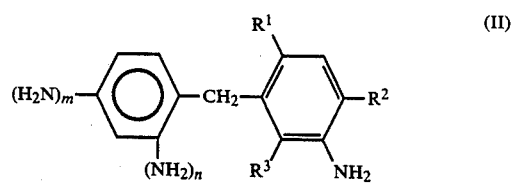

in which $R^1$, $R^2$, $R^3$, m and n have the meanings indicated above, optionally in the form of isomeric mixtures and optionally in admixture with minor quantities of the corresponding perhydrogenated diamines and/or optionally in admixture with minor quantities of the corresponding unhydrogenated aromatic diamines are phosgenated at $-20°$ C. to 250° C.

The invention further relates to the use of the new diisocyanates and diisocyanate mixtures as structural components for the production of polyurethanes by the isocyanate polyaddition process.

The starting materials for the process of the present invention are the diamines and diamine mixtures corresponding to the new diisocyanates and diisocyanate mixtures. These diamines and the main component(s) of these diamine mixtures correspond to formula (II). Diamines in which one of the groups $R^1$, $R^2$ or $R^3$ is a $C_1$-$C_4$ alkyl grup, particularly a methyl group are preferred.

The diamine mixtures used in the process of the present invention are in many cases position and/or stereo isomeric mixtures and the individual position isomers correspond substantially (i.e. to an extent of more than 60 wt. % and preferably more than 90 wt. %) to formula (II) while the remainder may be other amino benzyl cyclohexylamines which are alkyl substituted on the aromatic ring. In addition to these position isomers, the diamines and diamine mixtures to be used in the process of the present invention may have minor quantities of the corresponding perhydrogenated aromatic diamines and/or minor quantities of the unhydrogenated aromatic diamines present therein. By "minor quantities" is generally meant a proportion of perhydrogenated or unhydrogenated diamines amounting in each case to not more than 10 wt. % and preferably not more than 5 wt. % (based on the total quantity of diamine mixture). According to NMR spectroscopic findings, the main component or main components of the diamines or diamine mixtures to be used in the process of the present invention are almost exclusively asymmetric diamines corresponding to formula (II) in which the alkyl substituents are attached to the aromatic ring. The composition of the diisocyanates or diisocyanate mixtures of the present invention corresponds to that of the diamines and diamine mixtures used in their production.

Examples of diamine mixtures suitable for use as starting materials for the process according to the invention include commercial mixtures of diamines corresponding to the formula:

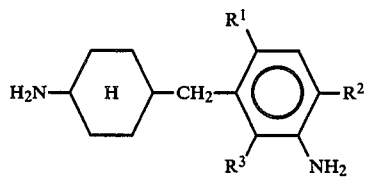

with up to 40 wt. %, based on the whole mixture, of diamines corresponding to the formula:

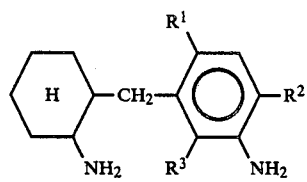

and optionally with up to 30 wt. %, preferably up to 20 wt. %, based on the whole mixture, of other aminobenzyl cyclohexylamines which are monoalkyl substituted on the aromatic ring. These commercial mixtures may also contain minor quantities of the corresponding unhydrogenated and/or perhydrogenated diamines.

Starting compounds which are particularly preferred for the process of the present invention are the position isomers corresponding to formula (II) in their pure form and constituting the main or minor components of the above-mentioned commercial diamine mixtures. Examples of such preferred starting compounds are: 4-(3-amino-4-methylbenzyl)cyclohexylamine, 2-(3-amino-4-methylbenzyl)-cyclohexylamine, 4-(5-amino-2-methylbenzyl)-cyclohexylamine, 2-(5-amino-2-methylbenzyl)-cyclohexylamine, 4-(3-amino-2-methylbenzyl)-cyclohexylamine and 2-(3-amino-2-methylbenzyl)-cyclohexylamine. The corresponding ethyl-, propyl- or butyl-substituted aminobenzyl cyclohexylamines and isomeric mixtures thereof meeting the compositional criteria of the above-described commercial diamine mixtures are also suitable.

Preparation of the diamines and diamine mixtures to be used in the process of the present invention is carried out by partial catalytic hydrogenation on the nucleus of the underlying aromatic diamines or by a two stage catalytic hydrogenation of the underlying dinitro compounds which represent the preliminary stage of the aromatic diamines. Preparation of such aromatic preliminary stages has been described, for example, in published European Patent Applications Nos. 0,024,665 and 0,046,556 and may be carried out by procedures analogous to those disclosed in these publications. For example, the above-mentioned pure position isomers or diamine mixtures having these isomers as their main component may be produced by condensation of p-nitrobenzyl chloride with p- or o-nitroalkyl benzenes followed by a two stage hydrogenation of the aromatic dinitro compound to the partially hydrogenated diamine. Such diamines may also be prepared by the condensation of o- or p-nitrobenzoyl chloride with o- or p-nitroalkyl benzenes, Clemmensen Reduction and subsequent hydrogenation on the nucleus of the aromatic diamines obtained as intermediate stage.

Catalytic hydrogenation of the aromatic diamines or dinitro compounds may be carried out by methods known in the art. Such methods include the chemical addition of 3 mols of hydrogen per mol of diamine or the reaction of 9 mol of hydrogen per mol of dinitro compound. The hydrogenation reaction is preferably stopped when 3 or 9 mol of hydrogen, respectively, per mol of starting compound have been used. Hydrogenation is carried out at 20°-300° C. under a pressure of 20-300 bar. When dinitro compounds are used as starting materials, it is advisable to carry out the initial hydrogenation of the nitro group within the temperature range of from 20°-150° C. (preferably from 30°-100° C.) at a pressure of from 20-150 bar (preferably from 70-140 bar) and subsequently to carry out the partial hydrogenation of aromatic hydrocarbon structure at a temperature of from 70°-300° C. (preferably from 120°-250° C.) at a pressure of from 70-300 bar (preferably from 120-240 bar). When aromatic diamino compounds are employed, hydrogenation is preferably carried out at a temperature of from 70° to 300° C. (preferably from 120° to 250° C.) at a pressure of from 70 to 300 (preferably from 120 to 240) bar. As to be seen from NMR-speotroscopic investigations the partially hydrogenated "H 6"-diamines consist almost exclusively of diamines whose alkyl substituents are linked to the aromatic ring.

The hydrogenation reaction is carried out in the presence of a hydrogenation catalyst used in a quantity of from 0.1-10 wt. %, preferably from 0.1 to 1 wt. % (relative to the quantity oF catalytically active metal on the one hand and diamino or dinitro compound on the other). Elements of the eighth subgroup of the Periodic System of Elements or catalytically active inorganic compounds of these elements (optionally mounted on inert carriers such as active charcoal, silica gel or in particular aluminum oxide) are examples of suitable catalysts. Ruthenium, platinum, rhodium, nickel and/or cobalt catalysts are particularly suitable, either in their elementary or in a chemically bound form. Ruthenium and catalytically active ruthenium compounds are particularly preferred. Examples of suitable ruthenium compounds include ruthenium dioxide; ruthenium tetroxide; barium perruthenite; sodium, potassium, silver, calcium and magnesium ruthenate; sodium perruthenate; ruthenium pentafluoride; ruthenium tetrafluorohydrate and ruthenium trichloride. If carrier substances are used for the catalysts, the metal content of the carrier catalyst is generally from 1–10 wt. %, preferably from 1–5 wt. %. The nature and quantity of catalyst to be used are not particularly significant since the hydrogenation reaction takes place by methods known in the art.

It is frequently advantageous to carry out the hydrogenation reaction in the presence of ammonia because ammonia suppresses unwanted deamination reactions and the formation of secondary amines as byproducts. Ammonia, if used, is generally introduced in quantities of from 0.1–30 wt. %, preferably from 5–10 wt. %, (based on the quantity of starting materials to be hydrogenated).

Hydrogenation may be carried out without using a solvent or in the presence of inert solvents. Low melting and liquid diamines are generally hydrogenated in the absence of solvent. High melting diamines and dinitro compounds are generally hydrogenated in the form of solutions. Suitable solvents for this purpose are organic compounds of low boiling point which are inert under the reaction conditions, particularly alcohols such as methanol, ethanol, n-propanol and i-propanol or ethers such as dioxane, tetrahydrofuran or diethyl ether, or hydrocarbons such as cyclohexane. Hydrogenation may be carried out continuously in a reaction tube or in a cascade of pressure vessels or, preferably, batch-wise in a stirrer autoclave. In the latter procedure, catalyst, the substance to be hydrogenated and optionally a solvent are introduced into the autoclave which is flushed repeatedly with inert gas and ammonia is optionally added. Hydrogen is then forced in and the mixture is heated to the reaction temperature and hydrogenated until the theoretically required quantity of hydrogen has been absorbed. After cooling of the reaction mixture and separation of the catalyst, the product of the process may be separated from unreacted starting product or perhydrogenated diamine by distillation.

In the process of the present invention, the new diisocyanates are prepared by phosgenation of the diamines described above or of their salts by known processes in the presence of an inert organic solvent (see Houben-Weyl, Methoden der Organischen Chemie, Georg Thieme Verlag Stuttgart (1952), Volume 8, 4th Edition, pages 122 et seq).

Particularly suitable salts to be phosgenated include the hydrochlorides and ammonium carbamates obtained by saturation of the diamine solutions with gaseous hydrogen chloride or carbon dioxide. In principle, other salts may also be phosgenated, for example, those obtained by neutralization of the diamines with acids which split off protons.

The selectivity of the phosgenation reaction depends to a large extent upon the amine concentration and the excess of phosgene. Phosgene is preferably introduced in a large molar excess and the diamine to be phosgenated is used in a highly dilute form. The molar excess of phosgene generally amounts to 100–2,000% (preferably 100–1,000%). The amine concentration, based on the total quantity of amines on the one hand and of solvents on the other, is from 0.1–15 wt. % (preferably from 5–10 wt. %).

The solvents used may be any inert organic liquids or mixtures thereof having a boiling point from 60°–250° C., i.e. halogenated hydrocarbons, aromatic compounds, hydro-aromatic compounds and their chlorine compounds. Examples of suitable solvents include xylene, mesitylene, chlorobenzene, dichlorobenzene, trichlorobenzene, chloronaphthalene and dichloroethane.

The reaction is either carried out in one stage by hot phosgenation at temperatures of from 100°–250° C. or in two stages by cold/hot phosgenation at temperatures of from −20° C. to 250° C. at normal pressure.

When the free amines are used as starting compounds (phosgenation of base), ammonium carbamic acid chloride is first prepared at temperatures of from −20° C. to 60° C., and this product then undergoes further reaction with phosgene at 20°–250° C. to form the diisocyanate.

Purification of the reaction products is carried out after dephosgenation, by evaporation of the solvent followed by distillation at reduced pressure.

The reaction products (i.e. the new diisocyanates of the present invention) are obtained in high yields as colorless, low viscosity liquids. These diisocyanates are valuable starting components for the production of polyurethanes by the isocyanate polyaddition process. The position and/or stereo isomerism of the new diisocyanates corresponds to the isomerism of the diamines used for phosgenation. It is generally not necessary to separate the mixtures obtained from the process of the invention into individual position and/or stereo isomers since the reaction products may be used directly.

The new diisocyanates of the present invention are particularly advantageous for the production of polyurethane lacquers, polyurethane elastomers or polyurethane foams. Appropriate isocyanate-reactive compounds, auxiliaries, additives and processes for the production of such polymer products are known to those in the art. The diisocyanates of the present invention may be used instead of or together with known polyisocyanates. It is particularly advantageous to use the new diisocyanates or diisocyanate mixtures for the production of polyurethanes of the type exemplified above by the prepolymer process.

The examples given below serve to illustrate the invention in more detail. All percentages are to be understood as percentages by weight unless otherwise indicated. Analysis of the isomeric distribution of the intermediate products and end products was carried out by gas chromatography.

EXAMPLES

Example 1

(1a) 250 g (1.18 mol) of the main fraction of polyamine mixture prepared in accordance with Example (7c) of European Patent Application No. 024,665, boiling at 198°–205° C./0.1 mbar and composed of 2.4% of 2,2'-diamino-4-methyl-diphenyl methane, 31.3% of 3,2'-diamino-4-methyl-diphenyl methane, 64.5% of 3,4'-diamino-4-methyl-diphenyl methane and 1.8% of undefined diamines and 25 g of ruthenium carrier catalyst (5% Ru on $Al_2O_3$) were introduced into a 0.7 liter stirrer autoclave. 25 g of ammonia were added after repeated rinsing of the autoclave with nitrogen and hydrogen. The reaction mixture was heated to 125° C. with stirring and 3.5 mol of hydrogen were reacted at 200 bar in the course of 12.5 hours. After separation of the catalyst, the crude product was distilled and the main fraction (Bp 110°–131° C./0.1 mbar) was rectified.

165 g of a diamine mixture boiling at 127°–131° C./0.1 mbar were obtained. According to gas chromatographic findings, this mixture was made up of 94.3% of 1-(1H-aminocyclohexyl-methyl)-3-amino-4-methylbenzene isomers (comprising more than 95% of isomers in which the cycloaliphatically bound amino group was in the 2- or 4-position), 2.8% of perhydrogenated starting diamines and 2.9% of unhydrogenated aromatic diamines. Due to the hydrogenation in the nucleus, the distribution of position isomers was substantially preserved.

(1b) 200 g of phosgene were dissolved in 700 ml of chlorobenzene at −5° to 8° C. A solution of 109 g of the diamine mixture from Example 1a) in 700 ml of chlorobenzene was slowly added drop-wise to the phosgene solution with stirring. The reaction mixture was then heated to 120° C. while phosgene was introduced at a moderate rate. Stirring was continued for an additional 2 hours under the same conditions. Excess phosgene was then removed by boiling under reflux for 1 hour and blowing nitrogen through the solution. After evaporation of the solvent at reduced pressure and distillation, 112 g of an isomeric mixture of 1-(1H-isocyanatocyclohexyl-methyl)-3-isocyanato-4-methylbenzene boiling at 118°–130° C./0.05 mbar and having an isocyanate content of 31%, a hydrolyzable chlorine content of 0.04% and a viscosity of 50 mPa·s/25° C. were obtained. The isomeric composition of this mixture was substantially similar to that of the starting product.

Example 2

(2a) A diamine mixture having the composition indicated below was prepared by dinitration of a condensate of 2-methyl-benzyl chloride and benzene followed by hydrogenation of the resulting dinitro compound in the manner described in European Patent Application No. 024,665. The composition of this mixture was as follows:

1% of 6,2'-diamino-2-methyl-diphenylmethane,
14.5 % of an isomeric mixture of 3,2'- and 5,2'-diamino-2-methyl-diphenylmethane,
0.9% of 6,3'-diamino-2-methyl-diphenylmethane,
7.9% of an isomeric mixture of 4,2'- and 6,4'-diamino-2-methyl-diphenylmethane,
75% of an isomeric mixture of which more than 80% was 3,4'- and 5,5'-diamino-2-methyl-diphenylmethane and the remainder was other diamino-2-methyl-diphenylmethanes, and
0.7% of undefined polyamines. 250 g (1.18 mol) of this diamine mixture were hydrogenated within 22 hours at 125° C. and 200 bar by a method analogous to that of Example (1a) using ruthenium carrier catalyst.

According to the gas chromatographic findings, the main fraction which boiled at 100°–146° C./0.1 mbar, was 41.0 g (15.5% of the theoretical amount) of the perhydrogenated diamine corresponding to the starting diamine, 190.9 g (74.2% of the theoretical amount) of (1H-aminocyclohexyl-methyl)-2-methylanilines corresponding to the starting diamine and 23.8 g (9.5% of the theoretical amount) of unchanged starting material. 2.1 g (0.8% of the theoretical amount) of distillation residue were obtained.

When fractional distillation was repeated at 138°–142° C./0.1 mbar, 171.1 g of (1H-aminocyclohexyl-methyl)-methyl anilines corresponding in their composition to the starting material and mixed with 4.6% of perhydrogenated diamine and 2.0% of starting product were obtained.

(2b) 109 g of the product of Example (2a) were dissolved in 700 ml of chlorobenzene. This solution was introduced drop-wise with vigorous stirring at 0°–8° C. into a solution of 200 g of phosgene in 700 ml of chlorobenzene. A viscous precipitate formed and was gradually dissolved when slowly heated while phosgene was introduced. The reaction mixture, which became clear at 105° C., was then boiled for 2 hours under reflux. The addition of phosgene was then stopped and dephosgenation was carried out by the introduction of nitrogen. After removal of the solvent by evaporation at reduced pressure, the diisocyanate mixture was purified by distillation. 104 g of diisocyanate boiling at 125°–129° C./0.04 mbar and having an isocyanate content of 31.0% and a viscosity of 70 mPa·s/25° C. were obtained. This diisocyanate had the following composition:

1.6% of 2-(6-isocyanato-2-methylbenzyl)cyclohexyl isocyanate,
9.1% of a mixture of 4-(4-isocyanato-2-methylbenzyl)-, 4-(6-isocyanato-2-methylbenzyl)-and 3-(6-isocyanato-2-methylbenzyl)-cyclohexyl isocyanate,
12.0% of a mixture of 2-(3-isocyanato-2-methylbenzyl)- and 2-(5-isocyanato-2-methylbenzyl)-cyclohexyl isocyanate and
77.3% of a mixture containing at least 80% of 4-(3-isocyanato-2-methylbenzyl)-and 4-(5-isocyanato-2-methylbenzyl)-cyclohexyl isocyanate.

Example 3

(3a) Using a method analogous to that of Example (1a), 250 g (1.18 mol) of 5,4'-diamino-2-methyldiphenylmethane were introduced into a 0.7 liter stirrer autoclave in the presence of 25 g of ruthenium carrier catalyst (5% Ru on Al$_2$O$_3$) and 25 g of ammonia at 125° C. The reaction mixture was hydrogented at 200 bar for 11.5 hours. After flash distillation at 120°–170° C. (0.2–0.5 mbar) followed by fine distillation, 165 g of diamine boiling at 130°–135° C./0.05 mbar were obtained. According to gas chromatographic analysis, this diamine was made up of 5% of 5,4'-diamino-2-methyldicyclohexyl methane, 94.4% of 4-(5-amino-2-methylbenzyl)-cyclohexylamine and 0.6% of 5,4'-diamino-2-methyl-diphenylmethane.

(3b) 200 g of phosgene were dissolved in 700 ml of chlorobenzene at −5° C. to 8° C. A solution of 109 g of the diamine mixture from Example (3a) in 700 ml of chlorobenzene was added drop-wise to the phosgene solution with stirring. A viscous solid separated and the mixture heated up to about 30° C. The temperature was slowly raised to about 110° C. with simultaneous introduction of 100 g of phosgene per hour until the solid substance had gone into solution. Stirring was then continued for an additional 3 hours while phosgene at 130° C. was introduced. The reaction mixture was dephosgenated and the crude product was distilled. 109 g of 4-(5-isocyanato-2-methylbenzyl)-cyclohexyl isocyanate boiling at 125°–127° C./0.1 mbar and having an isocyanate content of 31.0%, a hydrolyzable chlorine content of 0.02% and a viscosity of 75 mPa·s/25° C. were obtained.

Example 4

(4a) 250 g (1.18 mol) of 3,4'-diamino-4-methyldiphenylmethane and 25 g of Ru/Al$_2$O$_3$ (Ru content 5% by weight) were introduced into a 0.7 liter stirrer autoclave. After repeated rinsing with nitrogen and hydrogen, 25 g of liquid ammonia were introduced through a pump for liquefied gases. The autoclave was heated to 125° C. with stirring and hydrogenation was carried out at 200 bar until, after 16 hours, about 3.5 mol of hydrogen had been absorbed. The stirrer was then brought to a standstill, the autoclave was left to cool, the pressure was released, and the product was taken up in methanol. The catalyst was then filtered off and washed with methanol, and the methanol solutions were combined. After evaporation of the solvent and flash distillation at 0.1 bar and 100°–150° C., 254 g of a mixture which according to gas chromatographic analysis was made up of 219.5 g (85.3% of theory) of 4-(3-amino-4-methylbenzyl)cyclohexylamine and 34.0 g (12.9% of theoretical amount) of 3,4'-diamino-4-methyl-dicyclohexyl methane was obtained. An additional 150 g of 4-(3-amino-4-methylbenzyl)-cyclohexylamine was isolated by further distillation over a Vigreux column at 145°–146° C./0.1 mbar. The compositional analysis of the product $C_{14}H_{22}N_2$ was as follows:

| Calculated: | C | 77.06 | H | 10.10 | N | 12.84 |
|---|---|---|---|---|---|---|
| Measured: | C | 76.6 | H | 10.1 | N | 12.8 |

(all numerical values in %).

(4b) 94 g of phosgene at −5° C. were dissolved in 350 ml of anhydrous chlorobenzene. A solution of 52 g (0.238 mol) of 4-(3-amino-4-methylbenzyl)cyclohexylamine in 350 ml of anhydrous chlorobenzene was added drop-wise to the phosgene solution with vigorous stirring. The resulting suspension was heated to 65° C. until the solid dissolved (phosgene was introduced at the same time). Stirring was then continued for 3 hours at 120° C. After 2 hours dephosgenation, the solvent was distilled off at reduced pressure and the diisocyanate was purified by distillation at 133°–135° C./0.1 mbar. 58.3 g (90.7% of theoretical amount) of 4-(3-isocyanato-4-methylbenzyl)-cyclohexyl isocyanate having an isocyanate content of 31.0%, a hydrolyzable chlorine content of less than 0.01% and a viscosity of 50 mPa·s/25° C. were obtained.

Example 5

(5a) 25 g of ruthenium-aluminum oxide carrier catalyst and 250 g (1.106 mol) of a mixture of diamino-ethyl-diphenylmethane isomers prepared according to European Patent Application No. 46,556 (Example 5) were introduced into a 0.7 liter stirrer autoclave. The mixture of isomers had the following composition:
1.9% of a mixture of 2,2'-diamino-4-and 2,2'-diamino-6-ethyldiphenylmethane,
11.1% of 4,2'-diamino-2-ethyl-diphenylmethane,
20.1% of a mixture of 3,2'-diamino-2-, 3,2'-diamino-4- and 3,2'-diamino-6-ethyl-diphenylmethane,
66.1% of a mixture containing more than 80% of 3,4'-diamino-2-, 3,4'-diamino-2- and 3,4'-diamino-6-ethyldiphenylmethane and up to 20% of other diamino-ethyl diphenylmethanes, and
0.8 % of unknown triamines. After repeated rinsing with nitrogen and hydrogen, 25 g of ammonia were introduced and the reaction mixture was hydrogenated at 130° C. and 200 bar until 3.3 mol of hydrogen had been absorbed. The reaction mixture was then left to cool. The pressure was released and the product was taken up in methanol. The catalyst was removed by suction filtration. After removal of the solvent by distillation, the crude product was distilled twice at 0.05 mbar. 180 g of a diamine mixture boiling at 125°–136° C./0.05 mbar was obtained. The diamine mixture was made up of 93.6% of 1H amino-ethylbenzyl cyclohexylamine having an isomeric composition corresponding to that of the starting diamine, 2.9% of perhydrogenated starting material and 3.5% of unhydrogenated starting material.

(5b) A solution of 100 g of the diamine mixture from Example (5a) in 650 ml of chlorobenzene was added to a solution of 150 g of phosgene in 650 ml of chlorobenzene at −10° C. to −5° C. The reaction mixture was heated to the reflux temperature with introduction of phosgene. After further stirring for 90 minutes under the same conditions, the product was dephosgenated, concentrated by evaporation and distilled twice. 104 g of a diisocyanate boiling at 140°–144° C./0.1 mbar, 99.5% of which was various 1H-isocyanatoethylbenzyl-cyclohexyl isocyanate isomers corresponding to the starting material were obtained. The product was characterized by the following data:
Isocyanate value: 29.6%.
hydrolyzable chlorine content: <0.01%.
viscosity: 52 mPa·s/25° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate or isomeric mixture of diisocyanates corresponding to the formula

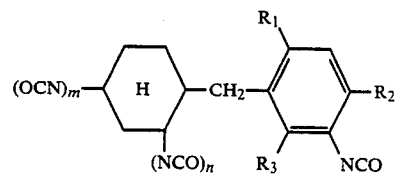

in which
$R_1$, $R_2$ and $R_3$ each represents hydrogen or an alkyl group having 1 to 12 carbon atoms, provided that two of the radicals $R_1$, $R_2$ and $R_3$ represent hydrogen and
m and n each represent 0 or 1 provided that $m+n=1$ and when m or n is zero, the free valence is filled with hydrogen.

2. The diisocyanate or isomeric mixture of claim 1 in which a minor quantity of a corresponding perhydrogenated diisocyanate and/or unhydrogenated aromatic diisocyanate is present.

3. The diisocyanate or isomeric mixture of diisocyanates of claim 2 in which $R_1$, $R_2$ or $R_3$ of the main component represents an alkyl group having 1 to 4 carbon atoms.

4. The diisocyanate or isomeric mixture of diisocyanates of claim 3 in which $R_1$, $R_2$ or $R_3$ represents a methyl group.

5. The diisocyanate or isomeric mixture of diisocyanates of claim 1 in which $R_1$, $R_2$ or $R_3$ of the diisocyanate or main component of the isomeric mixture of diisocyanates represents an alkyl group having 1 to 4 carbon atoms.

6. The diisocyanate or isomeric mixture of diisocyanates of claim 1 in which $R_1$, $R_2$ or $R_3$ of the diisocyanate or main component of the isomeric mixture of diisocyanates represents a methyl group.

7. The diisocyanate or isomeric mixture of diisocyanates of claim 1 in which n represents zero and $R_1$, $R_2$ or $R_3$ of the diisocyanate or main component of the mixture of diisocyanates represents an alkyl group having 1 to 4 carbon atoms.

8. The diisocyanate or isomeric mixture of diisocyanates of claim 7 in which $R_1$, $R_2$ or $R_3$ represents a methyl group.

9. The diisocyanate or isomeric mixture of diisocyanates of claim 1 in which m represents zero and $R_1$, $R_2$ or $R_3$ of the diisocyanate or main component of the mixture of dissocyanates represents an alkyl group having 1 to 4 carbon atoms.

10. The diisocyanate or isomeric mixture of diisocyanates of claim 9 in which $R_1$, $R_2$ or $R_3$ represents a methyl group.

* * * * *